United States Patent
Cleaver et al.

(10) Patent No.: US 7,407,795 B2
(45) Date of Patent: Aug. 5, 2008

(54) **METHOD FOR GROWING *CORDYCEPS SINENSIS* ON A SUBSTRATE AND NOVEL METHOD FOR HYBRIDIZING DIFFERENT STRAINS OF *CORDYCEPS SINENSIS***

(75) Inventors: Phillip D. Cleaver, Santa Cruz, CA (US); John C. Holliday, Santa Cruz, CA (US); Megan Loomis Powers, Huelo, HI (US)

(73) Assignee: John Holliday, Carson City, NV (US)

( * ) Notice: Subject to any disclaimer, the term of this patent is extended or adjusted under 35 U.S.C. 154(b) by 320 days.

(21) Appl. No.: 11/173,480

(22) Filed: Jul. 1, 2005

(65) Prior Publication Data

US 2006/0014267 A1    Jan. 19, 2006

Related U.S. Application Data

(60) Provisional application No. 60/588,204, filed on Jul. 15, 2004.

(51) Int. Cl.
*C12N 1/14* (2006.01)
*C12N 1/15* (2006.01)
*C12N 15/04* (2006.01)

(52) U.S. Cl. .............. 435/254.11; 435/254.1; 435/256.8; 435/440; 435/449; 435/454

(58) Field of Classification Search .............. 435/254.1, 435/256.8
See application file for complete search history.

(56) References Cited

OTHER PUBLICATIONS

Holliday et al. International Journal of Medicinal Mushrooms. 2004, vol. 6 (June), pp. 151-164.*
Wasser, et al. Medicinal Properties of Substances Occurring in Higher Basidiomycetes Mushrooms: Current Perspectives (Review),International Journal of Medicinal Mushrooms, (1999), p. 31-62. vol. 1, Begell House, Inc.
Zhu, et al. The Scientific Rediscovery of an Ancient Chinese Herbal Medicine: *Cordyceps sinensis* Part I, The Journal of Alternative and Complementary Medicine (1998) p. 289-303. vol. 4 No. 3, Mary Ann Liebert, Inc.
Zhu, et al. The Scientific Rediscovery of a Precious Ancient Chinese Herbal Regimen: *Cordyceps sinensis* Part II, The Journal of Alternative and Complementary Medicine, (1998), p. 429-457, vol. 4, No. 4, Mary Ann Liebert, Inc.
Mizuno, Medicinal Effects and Utilization of *Cordyceps* (Fr.) Link (Ascomycetes) and *Isaria* Fr. (Mitosporic Fungi) Chinese Caterpillar Fungi, "Tochukaso" (Review)*, International Journal of Medicinal Mushrooms, (1999), p. 251-261, vol. 1, Begell House, Inc.
Hsu, et al. A Comparison of the Chemical Composition and Bioactive Ingredients of the Chinese Medicinal Mushroom DongChongXiaCao, its Counterfeit and Mimic, and Fermented Mycelium of *Cordyceps sinensis*, Food Chemistry, (2002), p. 463-469, vol. 78, Elsevier Science, Ltd.
Furuya, et al. $N_6$-(2-Hydroxyethyl) Adenosine, A Biologically Active Compound From Cultured Mycelia of *Cordyceps* and *Isaria* Species, Phytochemistry, (1983), pp. 2509-2512, vol. 22, No. 11,Perfamon Press Ltd., Great Britain.
Wu, et al. Lead Poisoning Caused By Contaminated Cordyceps, A Chinese Herbal Medicine: Two Case Reports, The Science of the Total Environment, (1996), p. 193-195, Issue No. 182, Elsevier Science B.V.
*Cordyceps sinensis* (Berk.) Sacc. Link, C. Ophioglossoides (Ehr.:Fr.), Medicinal Fungi Monographs, Medicinal Mushrooms, p. 81-86.
Kirk, PM, Ainsworth & Bixby's Dictionary of the Fungi, 9th Ed., p. 41,43,114.
Acta Scientiarum Naturalium Universitatis Sunyatseni, Molecular Identification *Cordyceps sinensis*.pdf, (1999), vol. 38, No. 1, p. 01-0121-123, 1995-2005 Tsinghua Tongfang Optical Disc Co., Ltd. (English abstract).
Changkai, et al. Study on Nourishment of *Cordyceps sinensis* Mycelium (Microbiology Department of Shandong University, Jinan 250100), 1992, p. 129-133. (English abstract).
Shijiang, et al. Resources and Distribution of *Cordyceps sinensis* in Naqu Tibet, 1995, 18(4):171, p. 673-675, 1995-2005 Tsinghua Tongfang Optical Disc Co., Ltd. (English abstract).
Progress Cultivation *Cordyceps sinensis*, 1995-2005 Tsunghua Tongfang Optical Disc Co., Ltd. (in Chinese).

* cited by examiner

*Primary Examiner*—Vera Afremova
(74) *Attorney, Agent, or Firm*—Gabor L. Szekeres

(57) ABSTRACT

Two different strains of *Cordyceps sinensis* are placed at two different locations in a medium containing purified rattle snake venom and the two strains are allowed to grow until they meet in a boundary zone where a hybrid strain is formed due to exchange of genetic material. The hybrid strain is allowed to grow and is harvested and can be analyzed for the presence and quantity of desired medicinal substances. The amount of $N^6$-(2-hydroxyethyl)-adenosine in a *Cordyceps sinensis* strain or product sample is a reliable indicator of the overall health benefiting qualities of the strain or sample.

Figure 1:
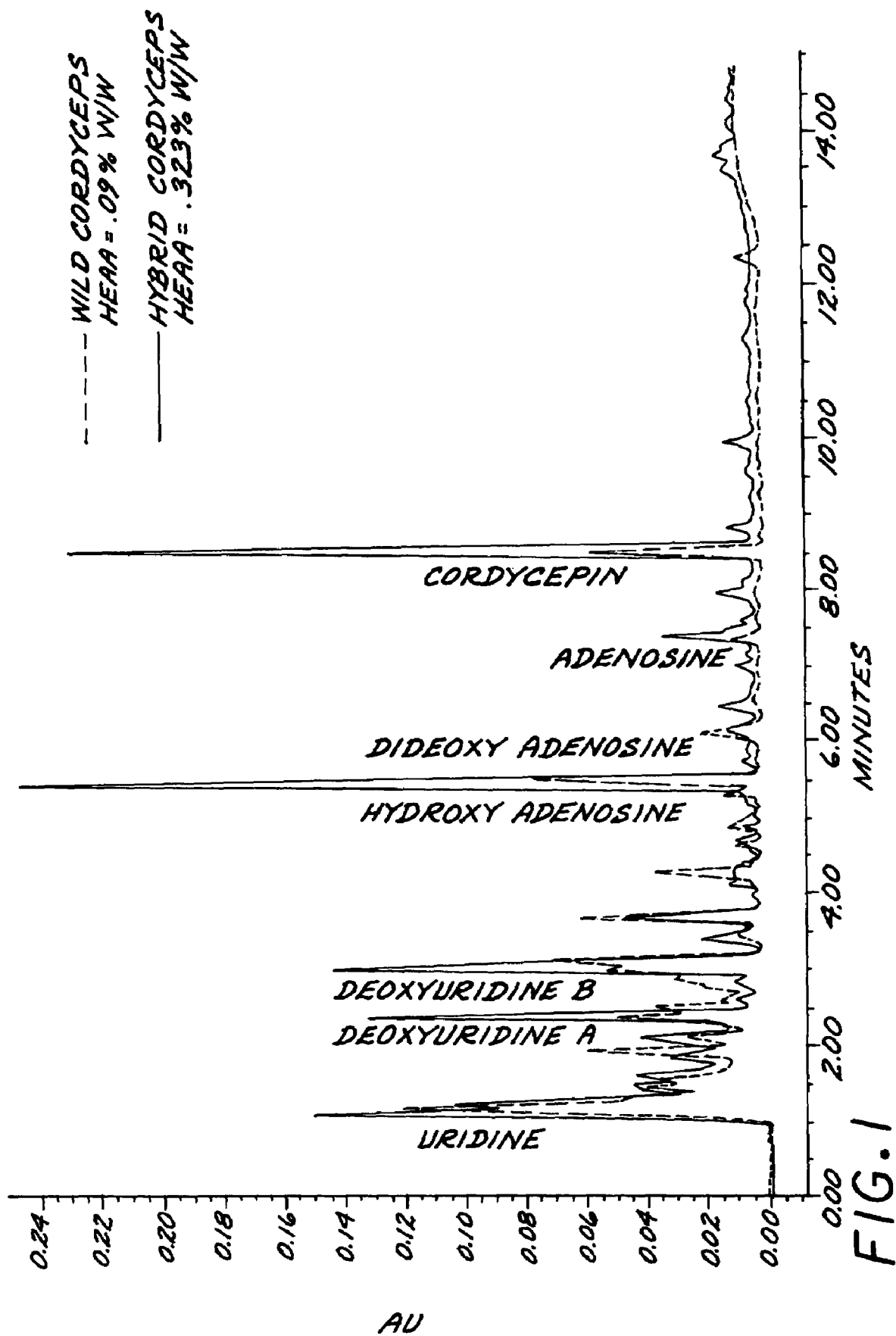

Strains of *Cordyceps sinensis*, are grown in a substrate at 20 to 22° C. at sea level atmospheric pressure for 28 to 30 days in diffuse light, and thereafter in an atmosphere containing approximately 50% of oxygen of the sea level atmosphere, at approximately 3° C. with exclusion of light, for approximately 15 to 20 weeks to provide a *Cordyceps sinensis* product that has the characteristic analytical signature of wild *Cordyceps sinensis* and includes substantial quantities of the health benefiting compounds of the strain found in the wild.

9 Claims, 1 Drawing Sheet

METHOD FOR GROWING *CORDYCEPS SINENSIS* ON A SUBSTRATE AND NOVEL METHOD FOR HYBRIDIZING DIFFERENT STRAINS OF *CORDYCEPS SINENSIS*

CROSS-REFERENCE TO PRIORITY PROVISIONAL APPLICATION

The present application claims the priority of provisional application Ser. No. 60/588,204, filed on Jul. 15, 2004.

BACKGROUND OF THE INVENTION

1. Field of the Invention

The present invention is directed to a novel method for growing *Cordyceps sinensis* in a substrate and to a novel method for hybridizing different strains of *Cordyceps sinensis* for the purpose of obtaining strains having the medicinal, health stimulating properties comparable or improved relative to strains of *Cordyceps sinensis* grown in the wild.

2. Brief Description of Background Art

*Cordyceps sinensis* is an ascomycetous fungus belonging to the Clavicipitaceae family. In nature *Cordyceps sinensis* colonizes and lives as a parasite on lepidopterous larvae. *Cordyceps sinensis* is normally found in the wild in the interior of China, Nepal, Tibet and in the Himalayas in an elevation range of approximately 2,000 to 6,000 meters.

*Cordyceps sinensis* has been known for a long time in the folk medicine of the Far East, mainly China and Japan, where it is respectively known as "Dong Chong Xia Cao" and "Tochukaso". In these countries the fungus, usually together with the caterpillar that it colonizes, is included in various soups for treating such diverse conditions as kidney and lung ailments and as a Yin/Yang (sexual) stimulator. Other species of the *Cordyceps* genus are also known to produce substances usable as antibiotics, immune stimulants, antiviral and antitumor agents.

Since approximately 1950 the worldwide demand for *Cordyceps sinensis*, to be used as a health stimulant, has grown substantially and attempts have been made to artificially cultivate it and other *Cordyceps* species as well. By the present the wild stocks of *Cordyceps sinensis* have been over-harvested. To supply the increased worldwide demand in the neutraceutical and pharmaceutical markets varieties of *Cordyceps sinensis* products have been made available in wide ranging and often questionable purity and quality. Even counterfeit products have been produced to supply the increasing demand.

Until the present investigation and discovery there was no universally accepted method of identifying the substances in *Cordyceps sinensis* which are responsible for its health benefiting effects, nor was there a standard method of measuring the quantity of one or more of these substances. It was also observed in the prior art and also in investigations made in connection with the present invention that various strains of *Cordyceps sinensis* provide or include the desired medicinal substances in varying amounts. Further, it was found in the investigation made in connection with the present invention that some commercially available nutraceutical products purportedly comprising *Cordyceps sinensis* contained none or only very little of the substances characteristic of a true *Cordyceps sinensis* sample.

In light of the foregoing there is a need in the nutraceutical and/or pharmaceutical arts for a standard method for establishing that a product indeed contains *Cordyceps sinensis*, for measuring the quantity of *Cordyceps sinensis* in that product, for developing strains of *Cordyceps sinensis* that produce the beneficial substances in substantial quantity, and for methods of growing *Cordyceps sinensis* in substantial quantities on a substrate. The present invention provides methods which satisfy these needs.

SUMMARY OF THE INVENTION

In accordance with one aspect of the present invention two different strains of *Cordyceps sinensis* are placed at two different locations in a medium containing purified rattle snake venom and the two strains are allowed to grow until they meet in a boundary zone where a hybrid strain is formed due to exchange of genetic material. The hybrid strain is allowed to grow and is harvested and can be analyzed for the presence and quantity of desired medicinal substances. It was found in accordance with the present invention that the amount of $N^6$-(2-hydroxyethyl)-adenosine in a *Cordyceps sinensis* strain or product sample is a reliable indicator of the overall health benefiting qualities of the strain or sample.

In accordance with another aspect of the present invention strains of *Cordyceps sinensis*, preferably the strain which contains high quantity of $N^6$-(2-hydroxyethyl)-adenosine and of related substances that are responsible for the health benefits provided by the fungus, are grown in a substrate at 20 to 22° C. at sea level atmospheric pressure for 28 to 30 days in diffuse light, and thereafter in an atmosphere containing approximately 50% of oxygen of the sea level atmosphere, at approximately 3° C. with exclusion of light, for approximately 15 to 20 weeks.

BRIEF DESCRIPTION OF THE DRAWING FIGURE

FIG. 1 shows the result of a high pressure liquid cliromatography analysis of the characteristic compounds of wildly grown *Cordyceps sinensis* and of a hybridized strain named *Cordyceps sinensis Alohaensis* which was developed in connection with the present invention.

DETAILED DESCRIPTION OF THE INVENTION

Numerous strains of *Cordyceps sinensis* and numerous samples of products purportedly or truly containing *Cordyceps sinensis* were analyzed by an analytical technique for the presence of certain nucleosides, particularly deoxynucleosides. The deoxynucleosides of particular interest in the samples or strains were adenosine, 3'-deoxyadenosine (also known as cordycepin) and $N^6$-(2-hydroxyethyl)-adenosine (HEA). The structures of these compounds are shown below.

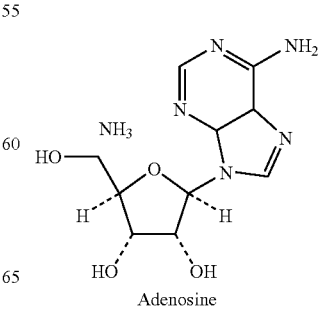

Adenosine

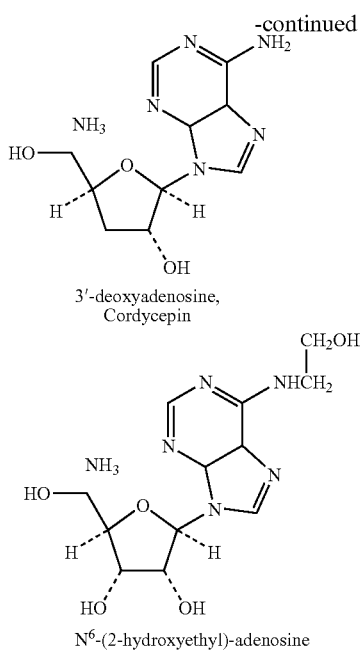

3'-deoxyadenosine, Cordycepin

N⁶-(2-hydroxyethyl)-adenosine

It was established in connection with the present invention that the presence and quantity of $N^6$-(2-hydroxyethyl)-adenosine is the most reliable indicator of the presence of genuine *Cordyceps sinensis* in a sample, and the quantity, as measured by weight-by-weight-percentage of this compound is the most reliable indicator of the overall health benefiting potency of the sample or strain.

Analysis of a sample containing *Cordyceps sinensis* can be performed by preparing trimethylsilyl derivatives of the sample, subjecting the trimethylsilyl derivatives to gas chromatography and determining presence of the nucleosides, especially of $N^6$-(2-hydroxyethyl)-adenosine by mass spectrometry of the gas chromatography fractions. An alternative method for analyzing the samples is high pressure liquid chromatography (HPLC) coupled with mass spectrometry detection. Precise details of these analytical techniques are provided below.

Gas Chromatography with Mass Spectronomy Detection

Trimethylsilyl Derivative Method.

Starting with well dried and finely ground powder of the raw test sample, 20 mg is added to 0.3 mL of derivatizing agent (BSTFA) and 0.3 mL of acetonitrile. This mixture is heated for 20 minutes at 60° C., which yields a trimethylsilyl derivative, which carries the material through gas chromatography (GC) for detection with a mass spectrometry (MS) detector. This test method is simple and quick, and when compared to results obtained from an authentic *C. sinensis* sample the method yields a positive/negative answer as to whether the test sample is actually *C. sinensis* or not. This method can also be used for quantification of the target compounds, although the next method is more accurate and more suitable for complete target compound quantification:

High Performance Liquid Chromatography Mass Spectronomy Detection

Powdered samples (2.0 g), were defatted by decanting with hexane (3×50 mL) and dried in vacuum. Samples were dissolved in 0.1M TBE (Tris-bo-rate-EDTA) buffer (pH 8.5 with 0.1N NH₄OH) (100 mL) and sonicated for 30 minutes at 40° C. An aliquot (10 mL) of the sample was then passed through a C-18 Sep-Pak that had previously been pre-equilibrated with 0.1 M TBE buffer (pH 8.5 with 0.1 N NH₄OH). The eluent was collected and the Sep-Pak further washed with the equilibration buffer to give a final eluent volume of 20 mL. After thorough mixing the sample was filtered through a 0.45 micron PVDF membrane and placed into suitable vials for HPLC-MS analysis. The chromatography was performed on a Waters 2695 separation module using a Wako Wakosil-II 5C18HG column (5 micrometer, 15 cm×4.6 mm i.d.) at 45° C. with gradient elution of H₂O:methanol (1 mL/min) from 22:3 to 77:23 in 19 minutes, then to 18:7 at 24 minutes and 27:23 at 39 minutes. The chromatographic eluent was passed into a Vestec particle-beam interface for solvent removal and particle atomization and then via TEFLON transfer line into the mass spectrometer using a helium carrier gas. Detection was performed on a Finnigan TSQ7000 triple-quadrapole mass-spectrometer in positive ion mode with full scan centroid data collection (50-1000 m/z). MS/MS experiments using an argon collision gas were used to verify the identity of unusual nucleotides for which no primary standards were available.

Development of Substrates

Substrates, which are improved relative to previously used substrates, for growing *Cordyceps sinensis* products of consistently high quantities of health benefiting substances, particularly the rare nucleosides, adenosine, 3'-deoxyadenosine (cordycepin) and $N^6$-(2-hydroxyethyl)-adenosine were also developed in connection with the present invention. In this connection it is noted that in prior art methods of cultivation in liquid substrate of nutrients a substantial portion of important health benefiting deoxynucleosides are lost because they are exuded by the mycelium into the liquid nutrient medium which is discarded after the mycelium is collected by filtration. In another prior art method of growing *Cordyceps sinensis* in a grain based solid substrate the extracellular nucleosides are retained but the material obtained for nutraceutical or pharmaceutical use tends to contain up to eighty percent residual grain.

The substrates developed in connection with the present invention were also designed to satisfy the United States Food and Drug Administration regulations that require the mycelium for human use to be grown on substrates that are themselves normally consumable human food sources. The nutrient substrates in which *Cordyceps sinensis* is grown and from which the nutraceutical or pharmaceutical product is collected should also satisfy consumer requirements for taste and appearance, namely the commercial product should have the characteristic *Cordyceps* taste. For example, a prior art substrate containing rye as the main component gives rise to a reasonably good quality *Cordyceps sinensis* product, but the taste of rye tends to mask the characteristic *Cordyceps* taste and therefore is not considered ideal in the consumer driven nutraceutical industry.

Thus, the optimal nutrient substrate found in connection with the present comprises white milo grain to which a small portion of millet grain has been added. The millet grain provides some essential ingredients required for optimum growth of *Cordyceps sinensis*. The optimal millet to white milo ratio has been found to be 1 part of millet to 4 parts of white milo. It was found that the *Cordyceps sinensis* product which can be obtained when the fungus is grown in this medium typically contains 96 to 97 percent mycelium and only 3 to 4 percent residual grain.

The ideal medium for solid substrate growth of *Cordyceps*, as determined in connection with the present invention, is as follows: 1 part white proso millet (husk on) to 4 parts of white milo (husk on), with the addition of 0.8% w/w of ground oyster shell and 1% w/w vegetable oil (peanut oil or soybean oil). Add water to equal 50% total moisture in the sterilized substrate. Precooking the grain mixture for 4 to 6 hours prior to sterilization tends to trigger a much faster growth response from the *Cordyceps*. On this medium, *Cordyceps* can be grown for long periods of time, allowing nearly complete conversion of the substrate to mycelium (96%+) and the full expression of secondary metabolites from the *Cordyceps*. The resultant *Cordyceps* grown on this substrate is about 3-4% residual grain or about 96-97 percent pure mycelium. The real benefit to this method of growing is the capture of the entire compliment of extracellular metabolites produced throughout the entire growth process.

In accordance with an important aspect of the present invention a method of growing *Cordyceps sinensis* is developed that results in a product that contains the above-mentioned adenosine-related nucleosides in quantities which are comparable to the quantities obtained from *Cordyceps sinensis* grown in the wild. As the novel method of the invention was developed it was found that *C. sinensis* produces a relatively large amount of free adenosine when grown at normal atmospheric oxygen levels and room temperatures. It also produces large quantities of uridine and guanidine but very little, if any, cordycepin and virtually no hydroxyethyl adenosine (HEA). It was found in accordance with the present invention that for the organism to produce the target medicinal compounds, it needs to be grown stressed through the absence of oxygen, a drop in temperature, and the total absence of light. However just growing *Cordyceps sinensis* under cold and anaerobic conditions from the start does not bring about the desired results, because when *C. sinensis* is grown under those conditions, it forms a yeast-like anamorph that has a very different chemical profile. Thus, it was found in accordance with the present invention that the fungus must first be grown hot and fast, then induced into converting its "summertime" metabolites into the target medicinal compounds. To get these target compounds a reasonably strict growth protocol was developed. It should be understood in connection with the following description that it discloses the parameters of the optimal growth conditions of the invention. However, it should also be understood that deviations from these optimal parameters up to plus or minus 10 percent, and more preferably only up to plus or minus 5 percent still produce acceptable results and are within the scope of the invention.

Thus, the optimal, most preferred growth conditions are as follows. After inoculation on to the millet/milo substrate, the *C. sinensis* is grown at 20-22° C., in diffuse light and at sea level atmospheric oxygen for 28-30 days. It is then moved into a specially controlled environmental chamber, where the oxygen content is dropped to 50% of normal atmospheric content. The remainder of the growth atmosphere is made up of nitrogen, carbon monoxide, and carbon dioxide. The temperature is dropped to 3° C., and all light is excluded. The fungus is held under these conditions for 15 to 20 weeks. This results in much of the adenosine being converted to cordycepin, dideoxyadenosine, and hydroxyethyl-adenosine. Many other unique nucleosides are also produced, with a final chemical profile identically, or substantially identically matching that of the wild *Cordyceps sinensis*, as can be shown by gas-chromatographic and/or HPLC analysis.

In accordance with another important aspect of the present invention a hybridization technique was developed whereby available strains of *Cordyceps sinensis* can be hybridized in an effort to obtain a hybrid strain that produces nearly the quantities of active ingredients found in the wild *Cordyceps sinensis*. The hybridization technique of the present invention involves nuclear fusion of two different strains of the fungus *Cordyceps sinensis*. This exchange of genetic material between the two strains is triggered by snake venom. The snake venom, preferably venom of the western diamond rattlesnake (*crotalus atrox*, available in a purified form from Sigma Scientific, Saint Louis Mo.), is added to the agar medium in quantities that alter the growth but do not prove toxic to the strains in question. This range of snake venom is from 10 to 30 mg per 300 mL of agar medium. The venom is not heat stable and must be added aseptically after sterilization of the medium. It is believed that standard state-of-the-art agars can be used in the hybridization process, however the preferred agar used for this hybridization is an Aloha Medicinals' proprietary agar named R7 Agar. It comprises malt extract, activated carbon, minerals, and humus which is the carbon-rich ash residue from a coal-burning industrial process. The exact composition of this agar is provided below. Again, in connection with the percentages and other parameters disclosed for the invented hybridization technique it should be understood that the disclosed process is the preferred one. However, deviations from these optimal parameters up to plus or minus 20 percent, and more preferably only up to plus or minus 10 percent still produce acceptable results and are within the scope of the invention.

Snake Venom R7 Agar Composition 2.1 L distilled water; 50 g light malt extract; 34 g agar; 10 g humus; 5 g activated carbon; 1 g $Mg_2SO_4$; 10 mL 1% KOH solution, and *c. atrox* venom as required.

Hybridization Technique

Petri dishes of R7 agar medium are inoculated with mycelium from two strains of the *Cordyceps* genus. These are usually two varieties of *C. sinensis*, although in connection with the present invention *C. sinensis* has been crossbred with other *Cordyceps* species such as *C. militaris*, *C. sobolifera*, and *C. ophioglosoides*. The different strains when inoculated together onto one petri dish will normally grow toward each other until they almost meet, at which point they form a zone of inhibition where neither strain can grow. In the absence of snake venom one strain may prove stronger than the other and overgrow the plate, but the strains remain genetically distinct: two different cultures residing in the same Petri dish.

With the addition of a sufficient quantity of snake venom to the agar, the two cultures grow toward each other until they meet and form their mutual zone of inhibition. This period of inhibition is short-lived however, for in only about 2 or 3 hours the colonies each start sending out mycelial strands into this no man's land, the zone of inhibition. These strands grow together and exchange nuclear material through their venom-weakened cell walls. They form a hybrid strain at this point of mutual contact which is a new strain distinctly different from either of the parent strains. Within about 4 hours after first forming the zone of inhibition, the hybridization is complete and the colonies resume rapid growth toward each other. They become three colonies, rather than the original two. There then exist in the same plate the original two colonies and a genetically distinct third colony of the hybrid.

A section of the newly formed hybrid is carefully removed from the original zone of inhibition at the time that the colonies begin to fuse. This is usually 3-4 hours after the initial meeting of the colonies. The hybrid is transferred to a new petri dish containing normal (non-snake venom) agar.

A quick method of determining hybridization is to inoculate a new dish containing normal agar with tissue samples from all three strains, the original two and the suspected hybrid. When hybridization has failed to occur, then the suspected hybrid will readily fuse, with either one or the other of the original colonies, proving that our suspected hybrid is not genetically distinct from the original. When hybridization has in fact taken place, there are then three distinct colonies in the petri dish and upon growth they form a mutual three-way zone of inhibition. Once a hybrid is confirmed, it is tested for growth parameters. If it appears to be a vigorous and hardy grower on the substrate of choice (usually and preferably the substrate described above), a quantity of mycelium is grown, harvested and analyzed for active ingredients. Through repeated experiments in this way a hybrid strain was created from the strains which are anamorphs of *Cordyceps sinensis*, obtained from the following institutes and identified as follows: Strain 1, identified as *Pacileomyces hepialus* (chen) obtained from Tong Hui Corporation in Nantong, China, and Strain 2, identified as *Gliocladium catenulatum* was obtained from Zhejiang University of Teclmology, Hangzhou, Zhejiang, China.

The new hybrid strain is easily grown in solid substrate culture, preferably in the substrate described above, with a potency greater than any other cultivated strain and at least equal to the highest quality wild *Cordyceps sinensis*. This new strain is named *Cordyceps sinensis Alohaensis*.

FIG. 1 shows the results of HPLC analysis, in accordance with the analytical method described above, of the characteristic compounds of *Cordyceps sinensis* and of the new strain *Cordyceps sinensis Alohaensis* which was developed in accordance with the hybridization method of the invention and grown in accordance with the method of the invention for growing *Cordyceps sinensis*. The line or plot that shows higher hydroxyethyl adenosine (HEA) content corresponds to *Cordyceps sinensis Alohaensis*, the other line or plot corresponds to natural, wild *Cordyceps sinensis*. The analysis of these samples show that *Cordyceps sinensis Alohaensis* grown in accordance with the method of the invention contains 0.323% w/w HEA and that wild *Cordyceps sinensis* contains 0.091% w/w of HEA.

The plot of wild *Cordyceps sinensis* is the basic signature of *Cordyceps sinensis* which is used for comparative purposes when determining whether a sample actually contains *Cordyceps sinensis*. An unknown sample is considered "authentic" *Cordyceps sinensis* if the plot of the unknown sample matches most points (>90%) on the plot of the natural wild *Cordyceps sinensis*.

What is claimed is:

1. A method of hybridizing two different strains of *Cordyceps sinensis* at distinct locations in a container and in a solid medium containing purified snake venom, the method comprising the steps of:

allowing the two strains to grow at the different locations in the solid medium containing purified snake venom until they meet in a boundary zone;

allowing exchange of nuclear material of the two strains in the boundary zone to form a hybrid strain;

allowing the hybrid strain to grow, and isolating the hybrid strain.

2. A method in accordance with claim 1 wherein the snake venom is rattle snake venom.

3. A method in accordance with claim 1 wherein the snake venom is venom of the western diamond rattlesnake *Crotalus atrox*.

4. A method in accordance with claim 1 further comprising the step of inoculating the isolated hybrid strain, the two different strains of *Cordyceps sinensis* at distinct locations in a container and in a solid medium lacking purified snake venom, allowing the strains to grow and observing a mutual three-way zone of inhibition thereby confirming the existence of a true hybrid strain.

5. A method in accordance with claim 2 further comprising the step of inoculating the isolated hybrid strain, the two different strains of *Cordyceps sinensis* at distinct locations in a container and in a solid medium lacking snake venom, allowing the strains to grow and observing a mutual three-way zone of inhibition thereby confirming the existence of a true hybrid strain.

6. A method in accordance with claim 3 further comprising the step of inoculating the isolated hybrid strain, the two different strains of *Cordyceps sinensis* at distinct locations in a container and in a solid medium lacking snake venom, allowing the strains to grow and observing a mutual three-way zone of inhibition thereby confirming the existence of a true hybrid strain.

7. A method in accordance with claim 1 wherein the medium comprises agar.

8. A method in accordance with claim 1 wherein the medium comprises materials in the ratio of approximately 1.9 to 2.2 L distilled water; approximately 45 to 55 g light malt extract; approximately 27 to 37 g agar; approximately 9 to 11 g humus; approximately 4 to 6 g activated carbon; approximately 0.9 to 1.1 g $Mg_2SO_4$ and approximately 9 to 11 mL 1% KOH solution.

9. A method in accordance with claim 8 wherein the medium comprises materials in the ratio of approximately 2.1 L distilled water; approximately 50 g light malt extract; approximately 34 g agar; approximately 10 g humus; approximately 5 g activated carbon; approximately 1 g $Mg_2SO_4$ and approximately 10 mL 1% KOH solution.

* * * * *